United States Patent [19]

Welters et al.

[11] Patent Number: 4,466,805

[45] Date of Patent: Aug. 21, 1984

[54] HAIRDYEING COMPOSITION AND METHOD

[75] Inventors: Reiner Welters, Darmstadt; Gernot Möschl, Weiterstadt; Hans-Dieter Allardt, Seeheim, all of Fed. Rep. of Germany

[73] Assignee: Merck Patent Gesellschaft mit Beschrankter Haftung, Darmstadt, Fed. Rep. of Germany

[21] Appl. No.: 180,060

[22] Filed: Aug. 20, 1980

Related U.S. Application Data

[63] Continuation of Ser. No. 907,475, May 19, 1978, abandoned.

[30] Foreign Application Priority Data

May 20, 1977 [DE] Fed. Rep. of Germany ....... 2722725

[51] Int. Cl.$^3$ .......................... D06P 3/04; A61K 7/42; A61K 7/44; A61K 7/021
[52] U.S. Cl. ......................................... 8/406; 8/408; 8/649; 424/DIG. 10; 424/59; 424/60; 424/61; 424/63; 424/70; 424/168; 424/174; 424/358; 424/361; 424/362; 424/365; 549/430
[58] Field of Search ................. 424/59, 63; 260/340.7, 260/340.9; 8/406, 405

[56] References Cited

PUBLICATIONS

Berichte, 1933, pp. 665 to 674, Fischer et al.

Primary Examiner—Dale R. Ore
Attorney, Agent, or Firm—Millen & White

[57] ABSTRACT

Compounds of the formula

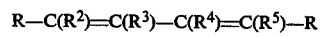

wherein R is —CHO, —CH(OR$^6$)$_2$, 1,3-dioxolan-2-yl, 4-methyl-1,3-dioxolan-2-yl or 1,3-dioxan-2-yl; R$^2$, R$^3$, R$^4$ and R$^5$ independently are hydrogen, methyl or ethyl; and R$^6$ is C$_{1-8}$ alkyl are highly useful as cosmetic active ingredients, e.g., as hair dyes and skin tanning agents. Compositions of these compounds with other active ingredients such as dihydroxyacetone are also quite effective.

10 Claims, No Drawings

HAIRDYEING COMPOSITION AND METHOD

This is a continuation, or application Ser. No. 907,475, filed May 19, 1978, now abandoned.

BACKGROUND OF THE INVENTION

The present invention relates to compounds which are useful as cosmetic active ingredients, e.g., hair dyes or skin tanning agents.

There is a need for substances and cosmetic preparations which tan the human skin without the need for irradiation by light of a suitable wavelength. All tanning of the skin which is caused by such radiation energy is linked with inflammatory processes in the tissue. These inflammatory processes can be suppressed to a minimum by using suitable light-screening filters, but irritation of the skin nevertheless still occurs and can lead, in particular, to delayed injuries.

Thus, the use of skin tanning agents is highly desirable in order to obviate the need for tanning light radiation while imparting the desired color to the skin. Only dihydroxyacetone has hitherto gained acceptance as a skin tanning agent. However, it is possible to achieve only a synthetic yellow-brown pigmenting using this compound. A red-brown coloration of the skin is much more desirable, for example, for people having a skin color which is in itself pale.

It is known that mucondialdehyde (compound of formula III herein; $R^2$ to $R^5$=H and $R^8$=CHO) in dilute aqueous solution can dye proteinaceous substances, and, in particular, also skin, a very fast and intense chocolate brown (Fischer, Löwenberg, Chem. Ber. 66, 665 [1933]). However, neither mucondialdehyde nor its purely aqueous solutions could hitherto be used as a skin tanning agent since the chemical process effecting the tanning proceeds very rapidly and, as a result, produces a blotchy or stripy coloration. The uniform skin coloration desired by consumers cannot be achieved.

The compound of formula III, herein, wherein $R^2$-$R^5$=H and $R^8$=—CH(OC$_2$H$_5$)$_2$ is also known per se and is disclosed in Fischer, Löwenberg, Chem. Ber. 66, 665 [1933]. However, the compound is not known to be useful as a cosmetic agent, e.g., as a skin tanning or hair dyeing active ingredient.

SUMMARY OF THE INVENTION

Accordingly, it is an object of this invention to provide compounds and cosmetic formulations which are suitable for use as skin tanning agents and especially without the need for skin irradiation.

It is another object of this invention to provide such compounds and cosmetic formulations which are suitable for use as hair dyes.

Upon further study of the specification and appended claims, further objects and advantages of this invention will become apparent to those skilled in the art.

These objects have been achieved by providing new compounds of formula I $$R^1—C(R^2)=C(R^3)—C(R^4)=C(R^5)—R^1 \qquad I$$

wherein $R^1$ is dimethoxymethyl, —CH(OR$^6$)$_2$, 1,3-dioxolan-2-yl, 4-methyl-1,3-dioxolan-2-yl or 1,3-dioxan-2-yl; $R^2$, $R^3$, $R^4$ and $R^5$ independently are hydrogen, methyl or ethyl; and $R^6$ is alkyl of 3-8 carbon atoms.

These objects have also been achieved by providing cosmetic compositions comprising at least one compound of formula II $$R^7—C(R^2)=C(R^3)—C(R^4)=C(R^5)—R^7 \qquad II$$

wherein $R^7$ is diethoxymethyl or $R^1$; and $R^2$, $R^3$, $R^4$ and $R^5$ independently are hydrogen, methyl or ethyl and cosmetically acceptable carriers and/or additives; and by providing compositions comprising at least one compound of formula III $$R^8—C(R^2)=C(R^3)—C(R^4)=C(R^5)—R^8 \qquad III$$

wherein $R^8$ is —CHO or $R^7$; and $R^2$ to $R^5$ are as defined above, and dihydroxyacetone. Conventional cosmetically acceptable carriers and/or additives, of course, may also be present.

This invention also relates to a method for tanning human skin which comprises treating the skin with an amount of a compound of formula II, or an amount of a composition containing a compound of formula III and dihydroxyacetone, effective to tan human skin.

This invention also relates to a method for dyeing human hair which comprises treating the hair with an amount of a compound of formula II, or an amount of a compound of formula III and dihydroxyacetone, effective to dye human hair.

DETAILED DISCUSSION

It has now been found that the compounds of formula I and the compositions containing the compounds of formula II can dye human skin a uniform red-brown color. The compositions containing the compounds of formula III also color the skin a uniform red-brown if they are used simultaneously with dihydroxyacetone. Since, as already mentioned, dihydroxyacetone, causes a yellow-brown coloration of the skin, the simultaneous use of the compounds of formula III with dihydroxyacetone makes it possible to produce various color gradations between yellow-brown and red-brown. The particular color shade obtained depends on the relative concentrations of the compound(s) of formula III and of dihydroxyacetone.

For formula I, $R^1$ is preferably dimethoxymethyl, 1,3-dioxolan-2-yl or 4-methyl-1,3-dioxolan-2-yl. When $R^1$ is —CH(OR$^6$)$_2$, $R^6$ is preferably an unbranched alkyl radical of 3-8, (e.g., 4-8 or 5-8 also) in particular of 3 or 4 carbon atoms, such as propyl or butyl. However, $R^6$ can also be branched alkyl of 3-8, in particular of 3 or 4 carbon atoms, for example isopropyl sec-butyl. Furthermore, other suitable alkyl radicals for $R^6$ include: pentyl, hexyl, heptyl, octyl, isopentyl and isohexyl.

The radicals $R^2$ to $R^5$ are preferably identical and are, in particular, hydrogen. When one of the radicals $R^2$ to $R^5$ is not hydrogen, it is preferred that the radicals $R^2$ and $R^5$ or $R^3$ and $R^4$ be identical.

Those compounds of the formula I in which at least one of the symbols $R^1$ to $R^6$ has one of the meanings individually mentioned above are preferred; those compounds of the formula I in which at least one of the symbols $R^1$ to $R^6$ has one of the meanings indicated above as being preferred are particularly preferred.

Some of these preferred groups of compounds can be characterized by the sub-formulae Ia to Iq below, which otherwise correspond to the formula I and in which the symbols not described in more detail have the meaning indicated for formula I, but wherein in Ia $R^3=R^4=H$;
in Ib $R^3=R^4=CH_3$;
in Ic $R^2=R^5=H$;
in Id $R^2=R^5=CH_3$;
in Ie $R^3=R^4=H$; and $R^2=R^5=CH_3$;
in If $R^3=R^4=CH_3$; and $R^2=R^5=H$;
in Ig $R^2=R^3=R^4=R^5=H$;
in Ih $R^2=R^3=R^4=R^5=CH_3$;
in Ii $R^1=$dimethoxymethyl, 1,3-dioxolan-2-yl or 4-methyl-1,3-dioxolan-2-yl;
in Ij $R^1=$dimethoxymethyl, 1,3-dioxolan-2-yl or 4-methyl-1,3-dioxolan-2-yl; and $R^3=R^4=H$;
in Ik $R^1=$dimethoxymethyl, 1,3-dioxolan-2-yl or 4-methyl-1,3-dioxolan-2-yl; and $R^3=R^4=CH_3$;
in Il $R^1=$dimethoxymethyl, 1,3-dioxolan-2-yl or 4-methyl-1,3-dioxolan-2-yl; and $R^2=R^5=H$;
in Im $R^1=$dimethoxymethyl, 1,3-dioxolan-2-yl or 4-methyl-1,3-dioxolan-2-yl; and $R^2=R^5=CH_3$;
in In $R^1=$dimethoxymethyl, 1,3-dioxolan-2-yl or 4-methyl-1,3-dioxolan-2-yl; $R^3=R^4=H$; and $R^2=R^5=CH_3$;
in Io $R^1=$dimethoxymethyl, 1,3-dioxolan-2-yl or 4-methyl-1,3-dioxolan-2-yl; $R^3=R^4=CH_3$; and $R^2=R^5=H$;
in Ip $R^1=$dimethoxymethyl, 1,3-dioxolan-2-yl or 4-methyl-1,3-dioxolan-2-yl; and $R^2=R^3=R^4=R^5=H$; and
in Iq $R^1=$dimethoxymethyl, 1,3-dioxolan-2-yl or 4-methyl-1,3-dioxolan-2-yl; and $R^2=R^3=R^4=R^5=CH_3$.

For formula II, $R^7$ is, in particular, diethoxymethyl. When $R^7$ is the same as $R^1$, it has, above all, the meanings for $R^1$ mentioned above as being preferred.

Those compositions which contain compounds of the formula II in which at least one of the symbols $R^7$ and $R^2$ to $R^5$ has one of the meanings individually mentioned above, and in particular one of the meanings indicated above as being particularly preferred, are preferred. Some of the groups of compounds contained in these preferred compositions can be characterized by the sub-formulae IIa to IIl below, which otherwise correspond to formula II and in which the symbols not described in more detail have the meanings indicated for formula II, but wherein in IIa $R^7=$dimethoxymethyl, diethoxymethyl, 1,3-dioxolan-2-yl or 4-methyl-1,3-dioxolan-2-yl;
in IIb $R^7=$dimethoxymethyl, diethoxymethyl, 1,3-dioxolan-2-yl or 4-methyl-1,3-dioxolan-2-yl; and $R^2=R^5=H$;
in IIc $R^7=$dimethoxymethyl, diethoxymethyl, 1,3-dioxolan-2-yl or 4-methyl-1,3-dioxolan-2-yl; and $R^3=R^4=H$;
in IId $R^7=$dimethoxymethyl, diethoxymethyl, 1,3-dioxolan-2-yl or 4-methyl-1,3-dioxolan-2-yl; and $R^2=R^5=CH_3$;
in IIe $R^7=$dimethoxymethyl, diethoxymethyl, 1,3-dioxolan-2-yl or 4-methyl-1,3-dioxolan-2-yl; and $R^3=R^4=CH_3$;
in IIf $R^7=$dimethoxymethyl, diethoxymethyl, 1,3-dioxolan-2-yl or 4-methyl-1,3-dioxolan-2-yl; and $R^2=R^3=R^4=R^5=H$;
in IIg $R^7=$diethoxymethyl;
in IIh $R^7=$diethoxymethyl; and $R^2=R^5=H$;
in IIi $R^7=$diethoxymethyl; and $R^3=R^4=H$;
in IIj $R^7=$diethoxymethyl; and $R^2=R^5=CH_3$;
in IIk $R^7=$diethoxymethyl; and $R^3=R^4=CH_3$; and
in IIl $R^7=$diethoxymethyl; and $R^2=R^3=R^4=R^5=H$.

For formula III, the radical $R^8$ is, in particular —CHO. When it is the same as $R^7$, it has, above all, the meanings for this radical indicated as being preferred.

Thus, according to this invention, those compositions which contain, in addition to dihydroxyacetone, at least one compound of formula III in which at least one of the symbols $R^8$ and $R^2$ to $R^5$ has one of the meanings individually mentioned above, and in particular one of the meanings indicated above as being preferred, are also preferred.

Some of these preferred compositions contain groups of compound which are characterized by the sub-formulae IIIa to IIIg below, which otherwise correspond to the formula III and in which the symbols not described in more detail have the meanings indicated for formula III, but wherein in IIIa $R^8=$—CHO, dimethoxymethyl, diethoxymethyl, 1,3-dioxolan-2-yl or 4-methyl-1,3-dioxolan-2-yl;
in IIIb $R^8=$—CHO or diethoxymethyl; in IIIc $R^8=$—CHO or diethoxymethyl; and $R^2=R^5=H$;
in IIId $R^8=$—CHO or diethoxymethyl; and $R^3=R^4=H$;
in IIIe $R^8=$—CHO or diethoxymethyl; and $R^2=R^5=CH_3$;
in IIIf $R^8=$—CHO or diethoxymethyl; and $R^3=R^4=CH_3$; and
in IIIg $R^8=$—CHO or diethoxymethyl; and $R^2=R^3=R^4=R^5=H$.

The compounds of formula I and the new compounds of the formulae II and III can be prepared by methods which are in themselves known and which are described, for example, for the tetraethylacetal of mucondialdehyde; compare Fischer, Löwenberg, Chem. Ber. 66, 665 [1933]. The chemical processes described below for the preparation of the starting compounds, and also of the compounds of formula I and of the new compounds of formulae II and III, are analogous processes which are carried out under reaction conditions which are in themselves known, such as are given in the literature (for example in standard works of preparative organic chemistry, such as HOUBEL-WEYL, Methoden der organischen Chemie (Methods of Organic Chemistry), Georg-Thieme-Verlag Stuttgart) for analogous reactions.

This invention furthermore relates to a process for the preparation of a compound of formula I, which consists essentially in reacting a compound of formula IV

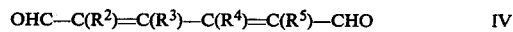
$$OHC-C(R^2)=C(R^3)-C(R^4)=C(R^5)-CHO \qquad IV$$

wherein $R^2-R^5$ are as defined above, with an acetalizing agent; in reacting a compound of formula V

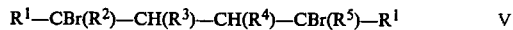
$$R^1-CBr(R^2)-CH(R^3)-CH(R^4)-CBr(R^5)-R^1 \qquad V$$

wherein $R^1-R^5$ are as defined above, with a dehydrobrominating agent; or in reacting a compound of formula VI

$$R^3-CO-CO-R^4 \qquad VI$$

wherein $R^3$ and $R^4$ are as defined above, with a compound of formula VII

$$(C_6H_5)_3P=C(R^9)-R^1 \qquad VII$$

wherein $R^9$ is $R^2$ or $R^5$ and $R^1$ is as defined above.

The compounds of formula IV are known (Fisher Löwenberg, Chem. Ber. 66, 665 (1933) or can be easily obtained from the compounds of formula VI by reaction with a Witting reagent, $(C_6H_5)_3P=CH—CHO$ in analogy to the methods and under reaction conditions as described in Koßmehl, Bohn, Chem. Ber. 107, 2791 [1974].

Examples of suitable acetalizing agents with which the compounds of formula IV can be reacted to produce the compounds of formula I are alcohols of the formula $R^{10}OH$ as well as ethylene glycol, propylene glycol and trimethylene glycol, optionally in the presence of orthoformates of formula VIII $$HC(OR^{10})_3 \qquad \text{VIII}$$

wherein $R^{10}$ is methyl or alkyl of 3–8 carbon atoms, or in the presence of acid catalysts, for example organic acids, above all organic carboxylic acids or sulphonic acids, such as alkanecarboxylic acids (for example formic acid, butyric acid palmitic acid or stearic acid), or, for example, benzenesulphonic acid, p-toluenesulphonic acid, α-naphthylsulphonic acid or camphorsulphonic acid. Inorganic oxides, such as $SiO_2$, $Al_2O_3$ or $ZrO_2$, which can be optionally partially hydrated, or mixtures thereof are also suitable catalysts.

Preferred reaction temperatures are room temperatures and slightly elevated temperatures up to about 45° C. A range from about $-10°$ to $+100°$ C. is also possible as the temperature interval. The water which forms during the reaction can be removed, if appropriate, by azeotropic distillation. For this it is necessary to add a water-immiscible solvent, for example benzene or toluene, to the reaction mixture.

The compounds of formula V are obtainable, for example, by treating the dialdehydes OHC—CH($R^2$)—CH($R^3$)—CH($R^4$)—CH($R^5$)—CHO with bromine in a solvent, for example, chloroform, at temperatures between about $-20°$ and about $-5°$ C., and then treating the reaction mixture with an alcohol $R^{10}OH$ at room temperature.

The compounds of formula V are converted into the desired compounds of formula I by reaction with a dehydrobrominating agent. Preferred dehydrobrominating agents include solid alkali metal hydroxides, in particular potassium hydroxide, but also tertiary organic bases, such as quinoline. The dehydrobromination is preferably carried out at elevated temperature, for example, between 90° and 160° C.; it is particularly advantageous to carry out the reaction at the boiling point of the reaction mixture, and if appropriate under reduced pressure.

The compounds of formula VI are known; preferred such compounds include glyoxal and diacetyl.

The compounds of formula VII can be prepared in a manner which is in itself known from triphenylphosphine and the halogenoacetals $R^9$—CHX—$R^1$ in the presence of a strong base, such as sodium hydride. The reaction of a compound of formula VI with a compound of formula VII is carried out under the conditions which are known for Wittig reactions.

Most of the compounds of formula VIII are known; new compounds of the formula VIII can be prepared by processes analogous to those for the corresponding known compounds.

The compositions according to this invention can be prepared as greasy or non-greasy creams, ointments, liquid formulations (lotions, tinctures or oils) or also as gels, from the compounds of formula II and in particular the compounds of formula I, or from the compounds of formula III, simultaneously using dihydroxyacetone, by adding suitable carriers and/or additives which are conventional in cosmetics. Examples of suitable carriers and/or additives are: hydrocarbons, such as solid or liquid paraffin, crystal oil, ceresin, ozokerite and montan wax; vegetable or animal oils, fats and waxes, such as olive oil, groundnut oil, sesame oil or almond oil, cacao butter, beeswax, mineral wax or carnauba wax, wool fat and spermaceti; fatty acids and fatty acid esters, such as stearic acid, palmitic acid, oleic acid, glycerol monostearate or distearate, glycerol monooleate, isopropyl myristate, isopropyl stearate and butyl stearate; alcohols, such as ethyl alcohol, isopropyl alcohol, cetyl alcoyol, stearyl alcohol, palmityl alcohol and hexyldodecyl alcohol; polyhydric alcohols, such as glycol, glycerol and sorbitol, which serve as humectants; emulsifiers of oil-in-water and water-in-oil systems, the commercially available ionic or non-ionic, cationic or anionic or ampholytic emulsifiers being possible; and thickeners such as methylcellulose, ethylcellulose or carboxymethylcellulose, polyacrylic acid, tragacanth, agar-agar and gelatin. Furthermore, additives such as perfumes, preservatives, skin care agents or physiologically acceptable dyestuffs can also, of course, be added, as required or as desired.

The compositions of this invention can additionally contain one or more UV absorbers, such as sodium 2-phenylbenzimidazole-5-sulphonate, sodium 3,4-dimethylphenylglyoxylate, 4-phenylbenzophenone, isooctyl 4-phenylbenzophenone-2'-carboxylate, p-methoxycinnamates, 2-phenyl-5-methylbenzoxazole, p-dimethylaminobenzoates, DL-tolylidene-camphor or DL-benzylidene-camphor.

The compositions of this invention contain the compounds of formula II in active and effective concentrations. In general, such compositions contain 0.03–20.0%, preferably 0.1–8.0%, most preferably 0.2 and 4.5% by weight of a compound(s) of formula II.

As already mentioned, this invention also relates to compositions which contain, in addition to carriers and/or additives which are conventional in cosmetics, at least one compound of formula III and dihydroxyacetone. Suitable carriers and/or additives include those mentioned above for formula I. The total content of active compounds in these compositions, when they are to be used for tanning skin, is between 0.1 and 30.0% by weight, preferably between 0.2 and 15.0% by weight and in particular between 1.0 and 12.5% by weight. The ratio between dihydroxyacetone and the compound(s) of formula III can vary over a wide range. As a rule, the proportion of dihydroxyacetone relative to the total amount of the tanning active compounds, is at least 40.0% by weight and at most about 99.85% by weight. Those agents are preferred in which the dihydroxyacetone makes up 55.0–99.5% by weight, and in particular 67.0–96.2% by weight (in each case relative to the total amount of the tanning substances). Compositions in which 0.03–0.30, preferably 0.04–0.20, parts by weight of compound(s) of formula III are present per one part by weight of dihydroxyacetone are particularly advantageous.

Although the final color shade is achieved only after several hours, frequently only on the next day when dihydroxyacetone is used alone, when the compositions of this invention, containing a compound of formula III as well as dihydroxyacetone, are used, final color shades are surprisingly achieved after only a short time, as a rule within about 30 minutes. The presence of a compound of formula III therefore has a greatly accelerating influence on the reaction on which the yellow-brown coloration of the skin by dihydroxyacetone is based.

It is particularly preferred to establish a pH value of about 2–7, in particular of about 5–6, in the compositions containing a compound of formula III as well as dihydroxyacetone by adding suitable buffering substances. Suitable buffer substances include: acids, preferably organic acids mixed with their corresponding alkali metal salts or ammonium salts. The alkali metal salts used are preferably the sodium salts; the ammonium salts used are those which are derived from amines which are customary in cosmetics, preferably secondary or tertiary amines, for example, from diethylamine, triethanolamine, bis-(2-hydroxypropyl)-amine, diethanolamine or morpholine, and also from ammonia. Preferred organic acids are hydroxycarboxylic acids (fruit acids), such as saccharic acids, tartaric acid, citric acid or lactic acid; but also include other acids, above all aliphatic acids, such as acetic acid, succinic acid, etc.; phosphoric acid and also hydrochloric acid.

As already mentioned, the cosmetic compositions described above are also useful for dyeing hair brown. For this use, they can then contain the active compounds in significantly higher concentrations than have been indicated for coloring skin. Hair colorants according to this invention contain, for example, between about 2.0 and 98.0% by weight, as a rule between about 3.0 and 60.0% by weight and in particular between 5.0 and 15.0% by weight, of compounds of formula II.

When they are to be used for dyeing hair on the head of a human, the compositions which contain at least one compound of formula III and dihydroxyacetone have similar compositions as indicated above for hair colorants containing compounds of formula II. However, the % by weight in this case refers to the total amount of active coloring substances. However, in contrast to skin coloring compositions, the proportion of compounds of formula III as a rule exceeds the proportion of the dihydroxyacetone present. Thus, for example, up to 99, preferably 5.0–60.0, in particular 5.0–20.0 parts by weight of compounds of formula III can be present per 1 part by weight of dihydroxyacetone. The compounds of formula III may also be used alone as hair colorants.

This invention also includes concentrates which contain a stabilizer and a carrier in addition to a relatively high content of compounds of formula II. These are also particularly valuable since they can be converted in a simple manner into cosmetic preparations desired by consumers by diluting and/or incorporating additional cosmetic substances. These stabilized active compound concentrates contain up to about 99% by weight, preferably, 5.0–60.0% by weight and in particular 5.0–20.0% by weight, of compounds of formula II in addition to 0.01–10.0% by weight, preferably about 1.0–3.0% by weight, of stabilizer. Suitable stabilizers, e.g., for stabilizing against chemical degradation, e.g., oxidation, i.e., for prolongation of activity of the active compound, include tertiary amines, preferably those which contain at least one relatively long carbon chain of more than 4 and up to 22 carbon atoms, and a total of more than 5 carbon atoms, such as dimethyldecylamine, diethyldecylamine, dimethyllaurylamine, dimethylmyristylamine, dimethylcetylamine, diethylcetylamine and dimethylstearylamine. Suitable carriers which are added to make the mixture up to 100% by weight are dry cosmetic carriers, above all triglycerides, the fatty acid radicals of which contain, in particular, 8–12 carbon atoms, liquid fatty acid esters of aliphatic alcohols and liquid paraffins.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 100 g of 2,5-diformyl-2,4-hexadiene, 1 g of ammonium nitrate, 192 g of triethoxymethane and 200 ml of dry ethanol are stirred at 20° for 48 hours; the mixture is neutralized with α-picoline; the solvent is distilled off; and, after purifying the residue by distillation, 1,1,6,6-tetraethoxy-2,5-dimethyl-2,4-hexadiene is obtained, b.p. = 135°–139°/0.2 mm Hg.

(b) The starting material can be obtained as follows: 70.4 g of trimeric glyoxal dihydrate, 636 g of (1-formylethylidene)-triphenyl-phosphorane and 1.8 l of dry dimethylformamide are stirred at 80° under nitrogen for 4 hours; the solvent is distilled off; the residue is extracted with 1,2-dichloroethane; the 1,2-dichloroethane is distilled off; the residue is dissolved in toluene, the solution is filtered; and, after distilling off the solvent from the filtrate, 2,5-diformyl-2,4-hexadiene is obtained as a residue, which can be further processed immediately.

The compounds of formula IV of Examples 2 to 6 which follow are obtainable analogously to Example 1b from the corresponding starting materials of formula VI by reaction with (1-formylethylidene)-triphenylphosphorane.

| EXAMPLE | COMPOUND OF FORMULA VI | COMPOUND OF FORMULA IV |
| --- | --- | --- |
| 2 | 2,3-dioxobutane | 2,5-diformyl-3,4-dimethyl-2,4-hexadiene |
| 3 | 1,2-dioxopropane | 2,5-diformyl-3-methyl-2,4-hexadiene |
| 4 | 1,2-dioxobutane | 2,5-diformyl-3-ethyl-2,4-hexadiene |
| 5 | 2,3-dioxopentane | 2,5-diformyl-3-ethyl-4-methyl-2,4-hexadiene |
| 6 | 3,4-dioxohexane | 2,5-diformyl-3,4-diethyl-2,4-hexadiene |

The compounds of formula IV of Examples 7 to 11 which follow are obtainable analogously to Example 1b from the corresponding starting materials of formula VI by reaction with formylmethylene-triphenylphosphorane:

| EXAMPLE | COMPOUND OF FORMULA VI | COMPOUND OF FORMULA IV |
| --- | --- | --- |
| 7 | 2,3-dioxobutane | 1,4-diformyl-2,3-dimethyl-1,3-butadiene |
| 8 | 1,2-dioxopropane | 1,4-diformyl-2-methyl-1,3-butadiene |

-continued

| EXAMPLE | COMPOUND OF FORMULA VI | COMPOUND OF FORMULA IV |
|---|---|---|
| 9 | 1,2-dioxobutane | 1,4-diformyl-2-ethyl-1,3-butadiene |
| 10 | 2,3-dioxopentane | 1,4-diformyl-2-ethyl-3-methyl-1,3-butadiene |
| 11 | 3,4-dioxohexane | 1,4-diformyl-2,3-diethyl-1,3-butadiene |

The compounds of formula IV of Examples 12 to 17 which follow are obtainable analogously to Example 1b from the corresponding starting materials of formula VI by reaction with (1-formylpropylidene)-triphenylphosphorane:

| EXAMPLE | COMPOUND OF FORMULA VI | COMPOUND OF FORMULA IV |
|---|---|---|
| 12 | 2,3-dioxobutane | 3,6-diformyl-4,5-dimethyl-3,5-octadiene |
| 13 | glyoxal | 3,6-diformyl-3,5-octadiene |
| 14 | 1,2-dioxopropane | 3,6-diformyl-4-methyl-3,5-octadiene |
| 15 | 1,2-dioxobutane | 3,6-diformyl-4-ethyl-3,5-octadiene |
| 16 | 2,3-dioxopentane | 3,6-diformyl-4-ethyl-5-methyl-3,5-octadiene |
| 17 | 3,4-dioxohexane | 3,6-diformyl-4,5-diethyl-3,5-octadiene |

The compounds of formula II of Examples 17a to 32 which follow are obtainable analogously to Examples 1a from the compounds of formul IV given in Examples 2–17 by reaction with triethoxymethane in ethanol:

| EXAMPLE | COMPOUNDS OF FORMULA II |
|---|---|
| 17a | 1,1,6,6-tetraethoxy-2,3,4,5-tetramethyl-2,4-hexadiene |
| 18 | 1,1,6,6-tetraethoxy-2,3,5-trimethyl-2,4-hexadiene |
| 19 | 1,1,6,6-tetraethoxy-3-ethyl-2,5-dimethyl-2,4-hexadiene |
| 20 | 1,1,6,6-tetraethoxy-3-ethyl-2,4,5-trimethyl-2,4-hexadiene |
| 21 | 1,1,6,6-tetraethoxy-3,4-diethyl-2,5-dimethyl-2,4-hexadiene |
| 22 | 1,1,6,6-tetraethoxy-3,4-dimethyl-2,4-hexadiene |
| 23 | 1,1,6,6-tetraethoxy-3-methyl-2,4-hexadiene |
| 24 | 1,1,6,6-tetraethoxy-3-ethyl-2,4-hexadiene |
| 25 | 1,1,6,6-tetraethoxy-3-ethyl-4-methyl-2,4-hexadiene |
| 26 | 1,1,6,6-tetraethoxy-3,4-diethyl-2,4-hexadiene |
| 27 | 1,1,6,6-tetraethoxy-2,5-diethyl-3,4-dimethyl-2,4-hexadiene |
| 28 | 1,1,6,6-tetraethoxy-2,5-diethyl-2,4-hexadiene |
| 29 | 1,1,6,6-tetraethoxy-2,5-diethyl-4-methyl-2,4-hexadiene |
| 30 | 1,1,6,6-tetraethoxy-2,3,5-triethyl-2,4-hexadiene |
| 31 | 1,1,6,6-tetraethoxy-2,3,5-triethyl-4-methyl-2,4-hexadiene |
| 32 | 1,1,6,6-tetraethoxy-2,3,4,5-tetraethyl-2,4-hexadiene |

EXAMPLE 33

114 g of adipodialdehyde are dissolved in 600 ml of chloroform at $-10°$ C.; 342 g of bromine, dissolved in 500 ml of chloroform, are added and the mixture is then stirred at 0° C. until it lightens in color. 800 ml of dry methanol are added; the mixture is stirred at 20° C. for 12 hours; excess sodium hydroxide solution is added; the organic phase is separated off and dried over $K_2CO_3$; the solvent is distilled off; and the residue is boiled with 80 g of sodium hydroxide in methanol at 130° and under 12 mm Hg for 30 minutes.

After purifying by distillation, 1,1,6,6-tetramethoxy-2,4-hexadiene is obtained, b.p.=102–104/6 mm Hg.

EXAMPLE 34

483 g of dichlorobutane, dissolved in 1.6 l of tetrahydrofuran, are added to a Grignard solution, prepared from 195 g of magnesium filings and 25 g of 1,4-dichlorobutane in 240 ml of dry tetrahydrofuran, in the course of 4 hours. The mixture is boiled for an additional 3 hours; the tetrahydrofuran is continuously replaced by toluene; 1,550 g of tributyl orthoformate are added at a reaction temperature of 100° C. in the course of 2 hours; 5 l of water are added to the suspension after an additional hour; the organic phase is separated off; the solvent is distilled off; and the residue is purified by distillation. 639 g of bromine are added to a mixture of 740 g of the fraction which boils at 148°–152° C./5 mm Hg, 500 g of calcium carbonate and 100 ml of dichloroethane at $-5°$ C. in the course of 2 hours. The orange-colored suspension is stirred at 20° C. for an additional hour; 200 ml of tributyl orthoformate are added; the mixture is stirred for an additional hour and filtered; the filtrate is washed with 1 l of 2% sodium hydroxide solution and then with water; the organic phase is dried with sodium sulphate; the solvent is distilled off; and the residue is added to a boiling mixture of 2 l of butanol and 475 g of sodium hydroxide. After 2 hours most of the solvent is distilled off; 1.5 l of water are added to the residue; the mixture is extracted with 1.5 l of cyclohexane; the organic phase is dried with sodium sulphate; the solvent is distilled off; and, after purifying the residue by distillation, 1,1,6,6-tetrabutoxy-2,4-hexadiene is obtained, b.p.=165°–172° C./0.06 mm Hg.

In the following examples of compositions of this invention, DHA=dihydroxyacetone; MA=1,4-diformyl-1,3-butadiene (=mucondialdehyde); MAA=1,1,6,6-tetraethoxy-2,4-hexadiene; and q.s.=quantum satis (sufficient quantity).

EXAMPLE A

| Aqueous alcoholic lotion: | |
|---|---|
| Concentrate containing 10% by weight of MAA 1% by weight of cetyldimethylamine and $C_8$–$C_{12}$ saturated fatty acid triglycerides to 100% | 3.0 g |
| Isopropyl myristate | 2.0 g |
| Diisopropyl adipate | 3.0 g |
| Propane-1,2-diol | 5.0 g |
| DHA | 2.0 g |
| Buffer solution of tri-sodium citrate and citric acid (about 0.01 molar) pH value: 5.5 | 10 g |
| Water, desalinated | 5 g |
| Perfume | q.s. |
| Propan-2-ol | to 100 g |

Use:

This mixture is applied thinly and uniformly, for example by means of a cottonwool pad, to the skin. After about 30 minutes, a coloration corresponding to the natural shade of tan has formed.

EXAMPLE B

| Aqueous alcoholic lotion | 0.1 g |
|---|---|
| MA | 10 g |
| Diisopropyl adipate | 5 g |
| Butane-1,3-diol | 5 g |
| Propane-1,2-diol | 1 g |
| Isopropyl myristate | 1 g |
| DHA | 55 g |
| 95% Ethanol | 55 g |
| Polyoxyethylene fatty acid ester | 3 g |

-continued

| | |
|---|---|
| (HLB value about 9) | |
| Buffer solution as in Example A | 10 g |
| Perfume | q.s. |
| Water, desalinated | to 100 g |

EXAMPLE C

| Aqueous alcoholic lotion | |
|---|---|
| 10% concentrate of MAA as in Example A | 4 g |
| Isopropyl myristate | 5 g |
| Spermaceti | 0.5 g |
| Diisopropyl adipate | 10 g |
| Water, desalinated | 8 g |
| Perfume | q.s. |
| Propanol-2-ol | to 100 g |

Use as for Example A; it is also possible to vary the color shade by combining, on the skin, any desired DHA cream with this agent.

EXAMPLE D

| Aqueous oily gel | |
|---|---|
| Polysaccharide, possessing structural viscosity (Xanthan Gum), 2% aqueous concentrate | 50 g |
| 10% concentrate of MAA as in Example A | 4 g |
| 2-Octyldodecanol | 2 g |
| Polyoxyethylene stearyl ether (HLB value about 17) | 10 g |
| Polyoxyethylene stearate (HLB value about 16) | 10 g |
| Succinic acid (0.1 molar) neutralized to the extent of about 50% with triethanolamine | 5 g |
| Decorative inorganic pearlescent pigment | 0.2 g |
| The Na salt of methyl 4-hydroxybenzoate | 0.3 g |
| The Na salt of propyl 4-hydroxybenzoate | 0.1 g |
| Allantoin | 0.2 g |
| Vitamin A + $D_3$ + E, water-soluble | 0.3 g |
| Perfume | q.s. |
| Water, desalinated | to 100 g |

Preparation: The surface-active agents are dissolved in water, while warming slightly, and all the ingredients, except for the Xanthan Gum concentrate, are stirred into this solution. This mixture is then homogeneously dispersed in the gel-like polysaccharide dispersion (planetary stirrer or kneader).

Use as for Example C

EXAMPLE E

| Tanning emulsion containing light protection agents (oil-in-water type) | |
|---|---|
| (a) 5% solution of MA in 95% ethanol | 3 g |
| Perfume | q.s. |
| (b) $C_8$-$C_{12}$ saturated fatty acid triglycerides | 3 g |
| p-tolylidene-camphor | 2 g |
| 2-octyldodecanol | 2 g |
| Polyoxyethylene stearyl/cetyl ether (HLB value about 8) | 8 g |
| Isopropyl myristate | 0.1 g |
| propyl 4-hydroxybenzoate | |
| (c) Propane-1,2-diol | 2 g |
| 70% sorbitol solution | 3 g |
| Allantoin | 0.2 g |
| The sodium salt of 3,4-dimethoxyphenyl glyoxylic acid | 3 g |
| 0.05 N succinic acid | 5 g |
| 0.05 N sodium hydroxide solution | 3.5 g |
| DHA | 2.5 g |
| Methyl 4-hydroxybenzoate | 0.2 g |
| Water, desalinated | to 100 g |

Preparation: The fat phase (b) and the aqueous phase (c) are warmed (melted, mixed) separately to about 75° C., after which (c) is stirred into (b) at a high speed of rotation. The substances of (a) are then stirred in at about 30°-35° C.

Use: The emulsion is applied to and spread on the skin thinly and uniformly; after about 30 minutes, a coloration equivalent to the natural shade of tan forms.

EXAMPLE F

| Tanning, light protection and insect repellent cream (oil-in-water type) | |
|---|---|
| (a) 1,1,6,6-tetrabutoxy-2,4-hexadiene | 1.5 g |
| 95% ethanol | 3.0 g |
| Decorative inorganic pearlescent pigment | 2.0 g |
| Perfume | q.s. |
| (b) Isopropyl isostearate | 3 g |
| $C_8$-$C_{12}$ saturated fatty acid triglycerides | 3 g |
| Isopropyl myristate | 2 g |
| Medium-viscosity liquid paraffin | 10 g |
| Ceresin wax | 2 g |
| Cetyl alcohol, sulphated to the extent of about 10% | 15 g |
| p-tolylidene-camphor | 2 g |
| 2-hydroxy-4-methoxybenzophenone | 3 g |
| Caprylic acid diethylamide | 5 g |
| Propyl 4-hydroxybenzoate | 0.05 g |
| (c) The triethanolammonium salt of 2-phenyl-benzimidazole-5-sulphonic acid, 50% in water | 2 g |
| Allantoin | 0.2 g |
| Buffer solution as in Example 1 | 3 g |
| DHA | 4 g |
| 70% sorbitol solution | 3 g |
| Propane-1,2-diol | 2 g |
| Methyl 4-hydroxybenzoate | 0.2 g |
| Water, desalinated | to 100 g |

Preparation: The fat phase (b) and the aqueous phase (c) are warmed separately to about 75° C. The hot homogeneous mixtures are then combined, while stirring. The ingredients from (a) are then stirred into the emulsion, which is still capable of flow, at about 35° C. and the entire cream is then homogenized in a triple roll mill.

Use: This formulation ensures effective light protection while simultaneously tanning the skin.

EXAMPLE G

| Tanning and skin care cream (water-in-oil type) | |
|---|---|
| (a) 10% concentrate of MAA as in Example A | 5 g |
| Decorative pearlescent pigment | 3 g |
| Perfume | q.s. |
| (b) Glycerol fatty acid ester and sorbitane fatty acid ester (mixture, HLB value about 4.5) | 5.4 g |
| Fatty acid ester, ethoxylated to a small extent | 6.6 g |
| Liquid Paraffin | 10 g |
| Ceresin wax | 3 g |
| Beeswax | 2 g |
| Vitamin A + $D_3$ + E + biotin in an oily solution | 0.5 g |
| Vitamin $B_6$ trispalmitate | 0.1 g |
| $C_8$-$C_{12}$ Saturated fatty acid triglycerides | 10 g |
| $C_8$-$C_{12}$ Partially unsaturated vegetable triglycerides | 2 g |
| Isopropyl myristate | 3 g |
| Propyl 4-hydroxybenzoate | 0.15 g |
| (c) DHA | 2.5 g |
| Allantoin | 0.2 g |
| Calcium D(+)-pantothenate | 0.2 g |
| 70% sorbitol solution | 3.5 g |
| Glycerol | 3 g |
| Methyl 4-hydroxybenzoate | 0.15 g |
| Water, desalinated | to 100 g |

Preparation: The fat phase (b) and aqueous phase (c) are warmed separately to about 70° C. and (c) is then stirred slowly into (b). The substances from part (a) are stirred in at about 35° C. The cream, which is still capable of flow and has the same temperature, is then homogenized on a triple roll mill.

Use: The skin care cream can also be used as a night cream and produces, after about 1 hour, a natural tan coloration.

EXAMPLE H

Two-component tanning agent for individual shading of the skin
1st component (greasy gel):

| | |
|---|---|
| (a) 10% concentrate of MAA as in Example A | 10 g |
| Inorganic pearlescent pigment | 1 g |
| Perfume | q.s. |
| (b) Stearic acid Supplement $B_6$ | 10 g |
| Candelilla wax | 3 g |
| Castor oil, hydrated (solid) | 3 g |
| Calcium stearate, very finely powdered | 0.5 g |
| $C_8$–$C_{12}$ saturated fatty acid triglycerides | to 100 g |

Preparation: The substances (b) are melted and mixed, and cooled, while stirring. The ingredients given under (a) are added at about 35° C. and then, if necessary, the mixture is homogenized.

2nd component (skin care cream)

| 2nd component (skin care cream) | |
|---|---|
| (a) Spermaceti | 3 g |
| Beeswax | 2 g |
| Liquid paraffin | 12 g |
| Ceresin wax | 3.5 g |
| Cetyl alcohol | 2 g |
| $C_8$–$C_{12}$ Saturated fatty acid triglycerides | 5 g |
| $C_8$–$C_{12}$ - Partially unsaturated fatty acid triglycerides | 3 g |
| Glycerol fatty acid ester and sorbitane Fatty acid ester | 9 g |
| Fatty acid ester, ethoxylated to a small extent | 6 g |
| Vitamin $B_6$ trispalmitate | 0.2 g |
| Vitamin A + $D_3$ + E + biotin, in an oily solution | 0.5 g |
| Cholesterol | 1 g |
| Propyl 4-hydroxybenzoate | 0.2 g |
| (b) Glycerol | 3 g |
| DHA | 5 g |
| 70% sorbitol | 5 g |
| Nicotinamide | 0.25 g |
| Panthenol | 0.25 g |
| Magnesium sulphate 7-hydrate | 0.7 g |
| Guaiazulene | 0.05 g |
| Methyl 4-hydroxybenzoate | 0.15 g |
| 2 N sodium citrate solution | 10 g |
| 2 N sodium hydroxide solution | 7.5 g |
| (c) Perfume | q.s. |

Preparation: The molten fat phase (a), warmed to about 70° C., is stirred with the aqueous phase (b), warmed to about the same temperature. The perfume is added at about 35° C. and the mixture is then homogenized (3 roll mill or similar device). Use: Component I is mixed with component II in an ointment dish (or mortar) in any desired ratio, according to the desired color shade, and the mixture is spread uniformly onto the skin. It is also possible to apply the two components one after another directly onto the area to be tanned.

EXAMPLE I

Two-component tanning agent (creams, oil-in-water type)

| Component I | |
|---|---|
| (a) MA | 0.5 g |
| Ethanol (95%) | 1.5 g |
| Perfume | q.s. |
| (b) $C_8$–$C_{12}$ Saturated fatty acid triglycerides | 3 g |
| Isopropyl myristate | 2 g |
| Liquid paraffin | 12 g |
| Solid paraffin | 2 g |
| Fatty alcohol polyglycol ether | 8 g |
| (c) 70% sorbitol | 3 g |
| Propane-1,2-diol | 2 g |
| Buffer solution as in Example 1 | 5 g |

The preparation is as in Example F.
Component II

The preparation is as in Example F.

Component II

As Component I, but without MA and ethanol. Instead, 5 g of water in the aqueous phase (c) are replaced by DHA. Use: This 2-component agent is particularly suitable for producing a tan according to individual wishes, as a rule first component I and then component II being applied.

EXAMPLE J

Tanning set
Component I (greasy gel):

| | |
|---|---|
| (a) 10% concentrate of MAA as in Example A | 15 g |
| Perfume | q.s. |
| Inorganic pearlescent pigment | 1 g |
| (b) $C_8$–$C_{12}$ Saturated fatty acid triglycerides | to 100 g |
| Isopropyl myristate | 10 g |
| Isopropyl stearate | 10 g |
| Carnauba wax | 5 g |
| Cetyl alcohol | 10 g |
| Beeswax | 5 g |
| Castor oil, hydrated | 10 g |

The preparation is as for component I from Example H.

Component II (aqueous gel):

| | |
|---|---|
| Polysaccharide, possessing structural viscosity (2% concentrate) | 50 g |
| Polyoxyethylene-20 stearate | 5 g |
| Polyoxyethylene-10 stearate | 2.5 g |
| Stearic acid Supplement $B_6$ | 0.3 g |
| Propane-1,2-diol | 5 g |
| Perfume | q.s. |
| Inorganic pearlescent pigment | 0.5 g |
| Succinic acid | 4.5 g |

Preparation

The surface-active agents, stearic acid, propanediol and succinic acid are dissolved in water, while warming. This mixture is stirred into the polysaccharide gel, which contains the pearlescent pigment. Finally, the perfume is added.

Component III

Any desired cream containing DHA, for example, component II from Example I, but with modification of the buffer composition. 20 g, per 100 g, of a 1 molar trisodium citrate solution additionally containing 2 g of 10% strength citric acid solution can be used as the buffer substance.

Component I is stirred with up to equal proportions by weight of component II and, after standing for a short time, the mixture is mixed with any desired amount of component III. Through this combination, a cream can be prepared which corresponds to personal requirements, for example for a weekly requirement, it being possible to correct the composition at any time.

EXAMPLE K

Tanning set containing liquid components
Component I

| Hydrophilic oil | |
|---|---|
| 10% concentrate of MAA according to Example 1 | 60 g |
| Polyoxyethylene-sorbitane fatty acid ester (HLB value 8) | 7 g |
| Isopropyl isostearate | 10 g |
| Isostearyl pentanoate | 10 g |
| $C_8$–$C_{12}$ Saturated fatty acid triglycerides | to 100 g |
| Perfume | q.s. |

Preparation: The components can be mixed without warming.

| Component II | |
|---|---|
| Polyoxyethylene-sorbitane stearate | 1.5 g |
| Stearyl alcohol polyglycol ether (HLB value about 12) | 5 g |
| Citric acid | 7.5 g |
| Water, desalinated | to 100 g |

Preparation: The substances are dissolved in water, while warming slightly.

Component III

| Component III Liquid, buffered emulsion | |
|---|---|
| (a) Liquid paraffin | 15 g |
| $C_8$–$C_{12}$ Saturated fatty acid triglycerides | 5 g |
| $C_8$–$C_{12}$ Partially unsaturated fatty acid triglycerides | 3 g |
| Cetyl alcohol | 2.75 g |
| Isopropyl myristate | 3 g |
| Vitamin $B_6$ trispalmitate | 0.1 g |
| Vitamin A + $D_3$ + E + biotin in an oily solution | 0.3 g |
| Sorbitane monostearate | 2 g |
| Polyoxyethylene-sorbitane monostearate | 3 g |
| Propyl 4-hydroxybenzoate | 0.05 g |
| (b) 70% sorbitol | 3 g |
| Glycerol | 2 g |
| DHA | 5 g |
| Allantoin | 0.2 g |
| Panthenol | 0.1 g |
| Nicotinamide | 0.1 g |
| Water, desalinated | to 100 g |
| Methyl 4-hydroxybenzoate | 0.2 g |
| Tri-sodium citrate (1 molar solution) | 20 g |
| Citric acid (10% solution) | 2 g |
| (c) Perfume | 2 g |

Preparation: The fat phase (a) and the aqueous phase (b) are warmed separately to about 75° C. and (a) is stirred into (b). The perfume is added (about 30°-40° C.) and, if appropriate, the mixture is homogenized.

Use: A tanning set containing 10 g each of component I and II (for example in dropper bottles) and 100 g of component III (for example in a squeeze bottle) can be used as follows: 5 drops of component I and 5 drops of component II, for example, are mixed and after a short time about 4 ml of component III are added. The mixture formed can be spread on the skin by means of a cottonwool pad. After about 30–60 minutes, a uniform natural attractive shade of tan forms on the skin.

EXAMPLE L

Hair colorant
Component I (basic mixture for liquid hair dyes)

| Dipropylene glycol | 20 g |
|---|---|
| Oleic acid | 30 g |
| Lactic acid | 4 g |
| Propan-2-ol | 10 g |
| Water, desalinated | to 100 g |
| Perfume | q.s. |
| Lauryl alcohol polyglycol ether, highly ethoxylated | 5 g |

| Component II | |
|---|---|
| 10% concentrate of MAA according to Example I | 40 g |
| Polyoxyethylene-fatty acid ester (HLB value about 9) | 10 g |
| $C_8$–$C_{12}$ Saturated fatty acid triglycerides | to 100 g |
| Perfume | q.s. |

Preparation: Both components are prepared by mixing the ingredients at room temperature.

Use: The parts are mixed in the ratio of about 1:1 before use and are spread on the hair to be dyed. After a time of action of about 30 minutes, a color shade between light chestnut brown and deep brown with a reddish luster is obtained, depending on the basic shade of the hair and the amount of colorant used. After shampooing, rinsing and drying, the hair has an excellent sheen, coupled with high elasticity (resilience).

EXAMPLE M

Hair colorant

| Component I | |
|---|---|
| MA, powdered | 4 g |
| Citric acid 1-hydrate, powdered | 7.5 g |
| Sodium citrate 2-hydrate, powdered | 6.5 g |
| Potassium sulphate, powdered | to 100 g |

Preparation: Dry powder mixing, for example, in a vertical screw mixer

| Component II | |
|---|---|
| Propanol | 25 g |
| Dipropylene glycol | 10 g |
| Carboxymethylcellulose (viscosity about 600 mPa.s, 1% in water) | to 100 g |
| Methyl 4-hydroxybenzoate | 0.3 g |
| Fatty alcohol polyglycol ether (highly ethoxylated) | 3 g |
| Perfume | q.s. |

Preparation: The preliminary solution of the polysaccharide is mixed with the other ingredients, while warming slightly.

The use, drying and other properties correspond to those in Example L.

EXAMPLE N

Hair colorant
Component I
As in Example M, but with the addition of 8 g–100 g of dihydroxyacetone in place of potassium sulphate.
Component II, as in Example M
Use as in Example M, but the color shade formed has more yellow constituents and appears somewhat brighter overall.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hairdyeing composition comprising an amount, effective to dye hair, of at least one compound of formula II $$R^7-C(R^2)=C(R^3)-C(R^4)=C(R^5)-R^7 \quad (II)$$

wherein $R^7$ is $-CH(OR^{12})_2$; $R^{12}$ is $C_{1-8}$ alkyl; and $R^2$, $R^3$, $R^4$ and $R^5$ independently are hydrogen, methyl or ethyl;

and an adjuvant acceptable in cosmetics.

2. A composition of claim 1, wherein $R^{12}$ is methyl, ethyl, propyl or butyl; and $R^2$, $R^3$, $R^4$ and $R^5$ are hydrogen.

3. A composition of claim 1, wherein the compound of formula II is 1,1,6,6-tetraethoxy-2,4-hexadiene.

4. A composition of claim 1 further comprising dihydroxyacetone.

5. A composition of claim 2 further comprising dihydroxyacetone.

6. A composition of claim 3 further comprising dihydroxyacetone.

7. A method of drying human hair which comprises applying to the hair an amount of a cosmetic composition of claim 1, 2 or 3 effective for dyeing human hair.

8. A method of dyeing human hair which comprises applying to the hair an amount of a cosmetic composition of claim 4 effective for dyeing human hair.

9. A method of dyeing human hair which comprises applying to the hair an amount of a cosmetic composition of claim 5 effective for dyeing human hair.

10. A method of dyeing human hair which comprises applying to the hair an amount of a cosmetic composition of claim 6 effective for dyeing human hair.

* * * * *